United States Patent
Tzuang et al.

(10) Patent No.: US 9,612,357 B1
(45) Date of Patent: Apr. 4, 2017

(54) DEVICE FOR RECEIVING/TRANSMITTING TERAHERTZ-GIGAHERTZ WAVE AND THE APPLICATION THEREOF

(71) Applicant: Archit Lens Technology Inc., Hsinchu (TW)

(72) Inventors: Lawrence Dah-Ching Tzuang, Goleta, CA (US); Yen-Ju Wu, Sheffield (GB)

(73) Assignee: ARCHIT LENS TECHNOLOGY INC., Hsinchu (TW)

( * ) Notice: Subject to any disclaimer, the term of this patent is extended or adjusted under 35 U.S.C. 154(b) by 0 days.

(21) Appl. No.: 15/232,333

(22) Filed: Aug. 9, 2016

Related U.S. Application Data (60) Provisional application No. 62/321,399, filed on Apr. 12, 2016.

(51) Int. Cl.
*G01J 5/02* (2006.01)
*G01V 8/00* (2006.01)
*G01N 22/00* (2006.01)
*G01N 21/17* (2006.01)

(52) U.S. Cl.
CPC ............ *G01V 8/005* (2013.01); *G01N 21/17* (2013.01); *G01N 22/00* (2013.01); *G01N 2021/178* (2013.01)

(58) Field of Classification Search
CPC ............ G01N 21/3586; G02F 2203/13; G01J 5/0837; G02R 29/0878
See application file for complete search history.

(56) References Cited

U.S. PATENT DOCUMENTS

| | | | | |
|---|---|---|---|---|
| 4,965,869 A | * | 10/1990 | Fortney | H01Q 19/10 343/772 |
| 5,023,594 A | * | 6/1991 | Wallace | G01S 7/032 333/250 |
| 5,867,120 A | * | 2/1999 | Ishikawa | H01Q 1/3233 342/175 |
| 6,317,095 B1 | * | 11/2001 | Teshirogi | H01Q 3/24 343/770 |
| 7,078,697 B2 | * | 7/2006 | Barker | B82Y 20/00 250/343 |
| 2005/0270247 A1 | * | 12/2005 | Kitamori | H01P 1/062 343/754 |
| 2010/0219851 A1 | * | 9/2010 | Trummer | F15B 15/2869 324/716 |
| 2010/0223983 A1 | * | 9/2010 | Trummer | F15B 15/222 73/114.29 |

* cited by examiner

*Primary Examiner* — Kiho Kim
(74) *Attorney, Agent, or Firm* — WPAT, PC; Justin King (57) ABSTRACT

The present invention provides an electromagnetic wave receiving/transmitting device and the application thereof. The electromagnetic wave receiving/transmitting device of the present invention can effectively receive up to 80 to 500 GHz of terahertz electromagnetic waves. The electromagnetic wave receiving/transmitting device of the present invention further achieves the application of terahertz imaging. The physical package of the electromagnetic wave receiving/transmitting device of the present invention is capable of effectively absorbing external and internal noise of electromagnetic waves to significantly reduce noise, and thereby achieving the application of terahertz imaging.

38 Claims, 9 Drawing Sheets

DEVICE FOR RECEIVING/TRANSMITTING TERAHERTZ-GIGAHERTZ WAVE AND THE APPLICATION THEREOF

FIELD OF THE INVENTION

The present invention relates to electromagnetic wave receiving/transmitting devices, and in particular, to terahertz (THz) electromagnetic wave receiving/transmitting devices and applications thereof. In particular, the present invention uses an efficient THz electromagnetic absorber for the housing material, which greatly reduces both the interior and exterior electromagnetic noises, thereby achieving the purpose of THz electromagnetic wave receiving/transmitting and imaging.

BACKGROUND OF THE INVENTION

Terahertz (THz) waves for electromagnetic radiations is a frequency unit in the range of 0.3 to 3 THz, suitable for applications with frequencies bounded between a high frequency edge (300 GHz) of millimeter wave band and a low frequency edge (3000 GHz) of far-infrared spectral band edge, where the wavelengths corresponding to this frequency range are from 1 mm to 0.1 mm (or 100 µm), respectively. At present, the THz radiation has reached the following consensus internationally: THz is a new radiation source with many unique advantages. THz technology is a very important cross frontier, offering opportunities for new technological innovations, economic developments, and national security applications. Aside from its vast range of applications, the reasons THz technology is attracting widespread attentions is firstly, because the THz spectrum (including the transmission spectrum and the reflection spectrum) of substances contains a wealth of physical and chemical information, therefore this frequency spectrum contains important information of the nature and structures of substances; secondly, because a THz light source has unique transmission and reflection properties compared to traditional light sources.

In recent years, thanks to the rapid development of ultrafast laser technology, excitation light source for THz pulse have become more stable and reliable, fueling the grounds for further studies of THz technology. In addition, THz imaging technology has been highly valued by governments, research institutions, universities and other research institutions. In addition to the development of pulsed THz imaging technology, continuous-wave THz imaging technology, including active and passive imaging techniques, are the subjects of extensive research. In particular, THz imaging techniques have been, to some extent, put to use in security detections and security inspections in key sectors. Meanwhile, various kinds of THz radiation sources, detectors, and some elements with critical functions are also being rapidly developed, which laid the foundation for the applications of the THz technology in chemistry, biology, material, petroleum, chemical engineering, communications, and other fields particularly in the military and security.

Therefore, there are considerable needs for THz electromagnetic wave systems with built-in high absorption housings, such that these systems effectively transmits/receives THz electromagnetic waves while eliminating the interference from unwanted noises.

SUMMARY OF THE INVENTION

In view of the background of the invention above, and to address the needs in the industry, the present invention proposes an electromagnetic wave receiving/transmitting device that overcomes the outstanding issues in the conventional art as mentioned above.

One objective of the present invention is to provide an electromagnetic wave propagation cavity capable of absorbing stray electromagnetic waves generated from outside as well as inside of the electromagnetic wave propagation cavity, thereby eliminating interferences from the noises and maintaining a high signal-to-noise ratio.

Another objective of the present invention is to provide an electromagnetic wave receiving/transmitting device that transmits/receives electromagnetic waves through the electromagnetic wave propagation cavity to a sensing region. The transmitting/sensing region may be integrally formed with the electromagnetic wave propagation cavity inside the electromagnetic wave receiving/transmitting device. As such, high-frequency electromagnetic waves can be effectively detected, and applications for imaging devices are made possible. The structural robustness of the electromagnetic wave receiving/transmitting device is high enough to protect and secure the expensive elements therein.

Still another objective of the present invention is to provide an electromagnetic wave receiving/transmitting device that can be applied to reflective and/or transmissive electromagnetic wave imaging method(s). Arranging at least one high-frequency electromagnetic wave emitter and the electromagnetic wave receiving/transmitting device on the same side or opposite sides enables reflective or transmissive imaging methods, respectively, thus offering high design flexibility.

DETAILED DESCRIPTION OF THE INVENTION

The present invention is directed to an electromagnetic wave receiving/transmitting device. In order to facilitate a thorough understanding of the present invention, detailed structures and their elements and steps of methods are provided in the following descriptions. It should be apparent that the present invention can be practiced without the specific details well known to those with ordinary skilled in the art of electromagnetic wave reception and transmission. On the other hand, well-known structures and their elements are not described in detail to prevent imposing unnecessary limits to the present invention. In addition, in order to provide a clear description and for those with ordinary skill in the art to understand the contents of the present invention, various elements in the diagrams are not drawn to scale; the sizes of some may be exaggerated relative to others; and some details that are not relevant to the present invention are completely omitted for conciseness. Reference will be made in details to preferred embodiments of the present invention below. The present invention may be generally practiced in other embodiments, and the scope of the present invention is not limited as such, but rather defined by the appended claims.

Figure 1A:
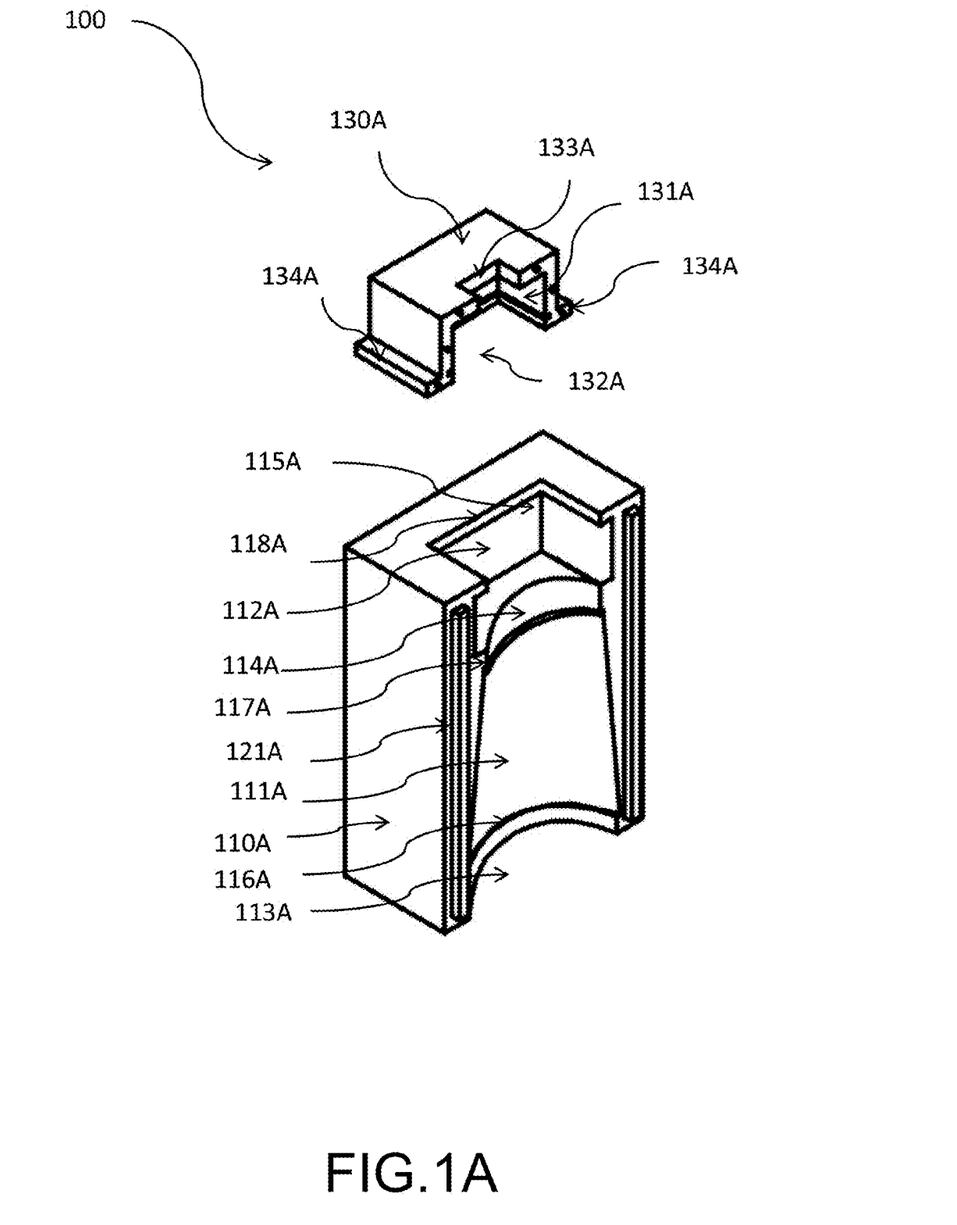
FIG. 1A and FIG. 1B is an exploded view of an electromagnetic wave receiving/transmitting device in accordance with the present invention.
Figure 1B:
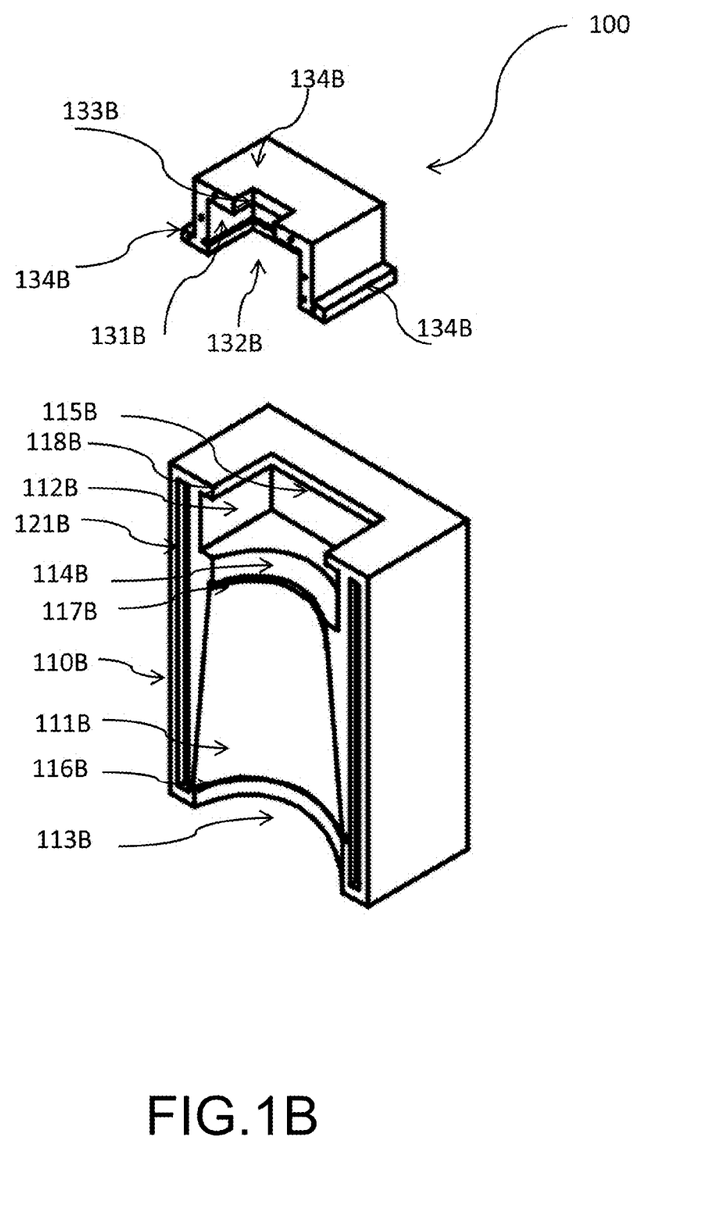
Figure 2A:
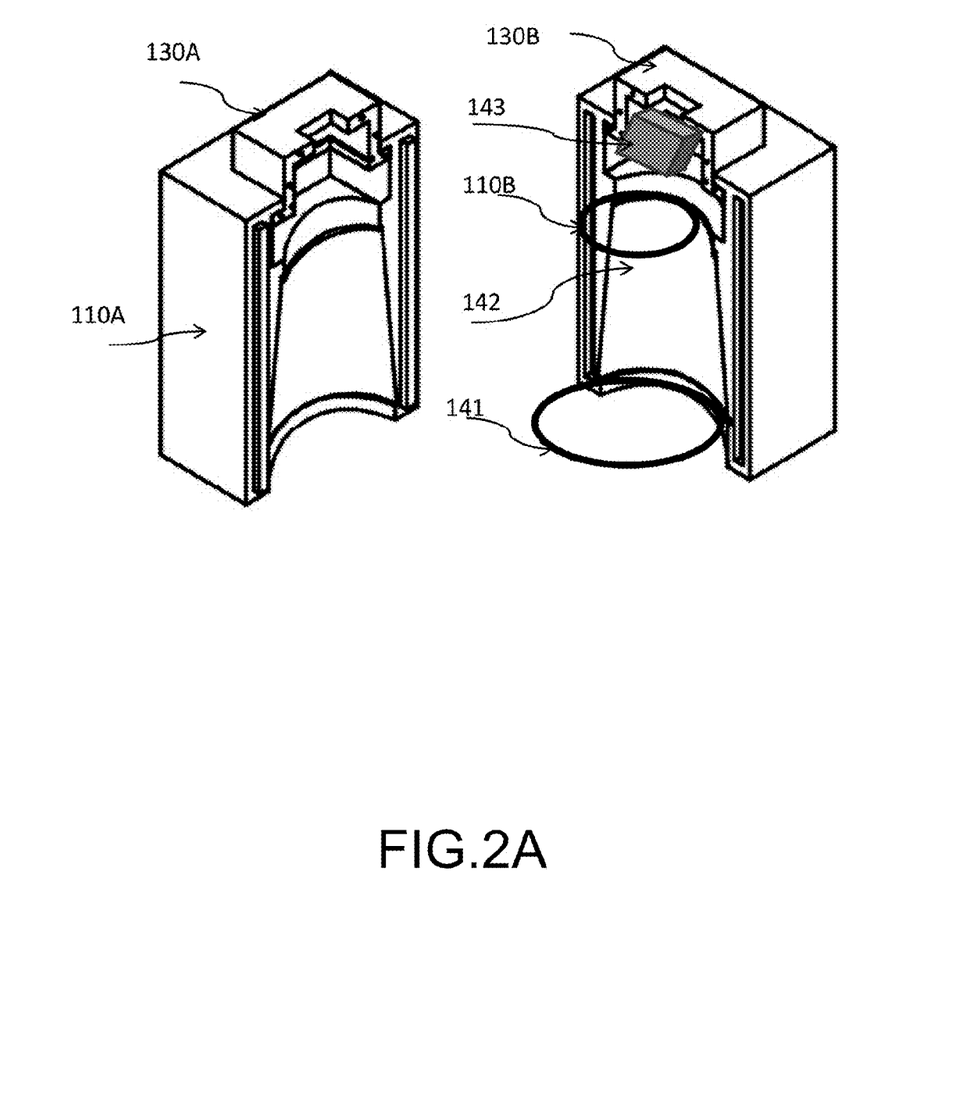
FIG. 2A is an exploded view of a pushed-out electromagnetic wave receiving/transmitting device in accordance with the present invention.
Figure 2B:
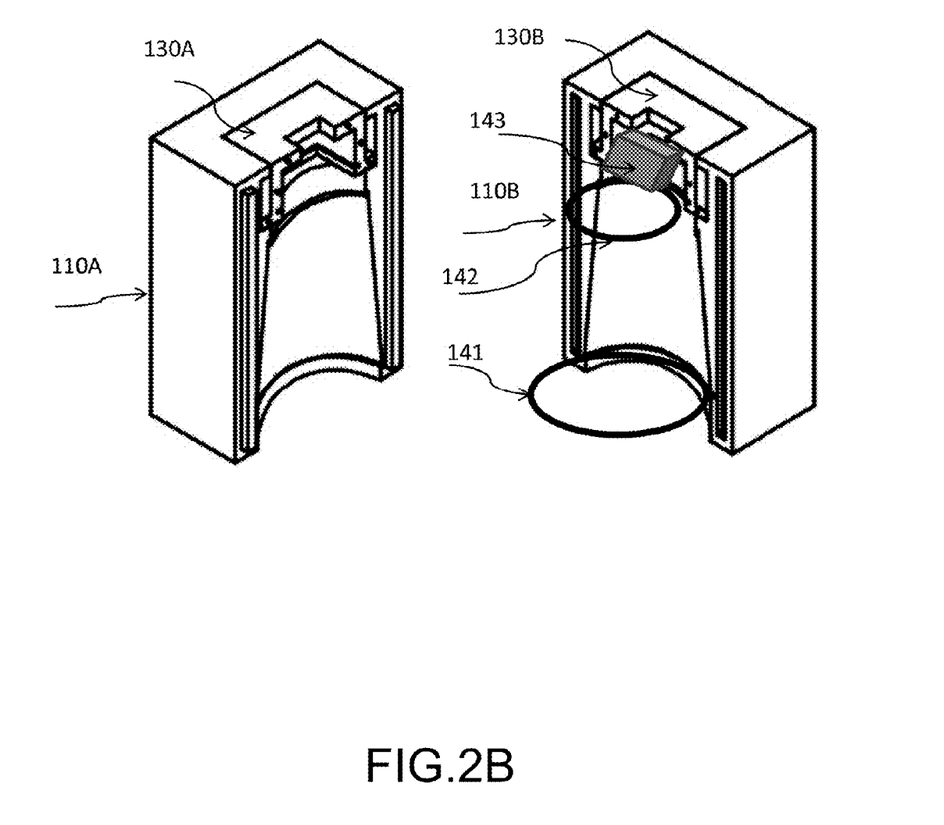
FIG. 2B is an exploded view of a pushed-in electromagnetic wave receiving/transmitting device in accordance with the present invention.
Figure 3A:
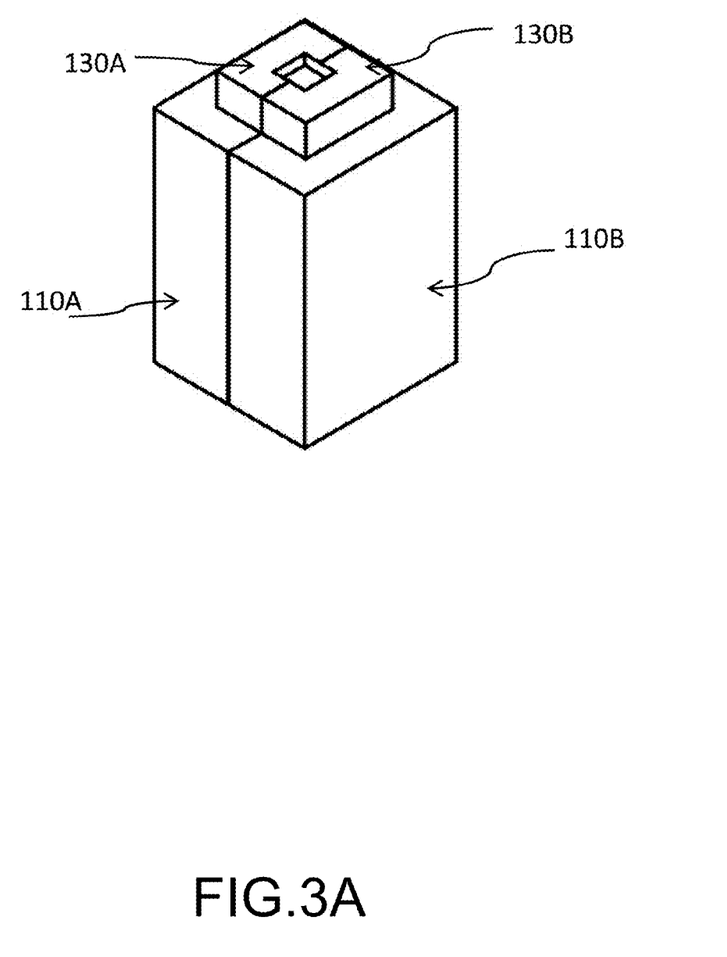
FIG. 3A is an isometric view of a pushed-out electromagnetic wave receiving/transmitting device in accordance with the present invention.
Figure 3B:
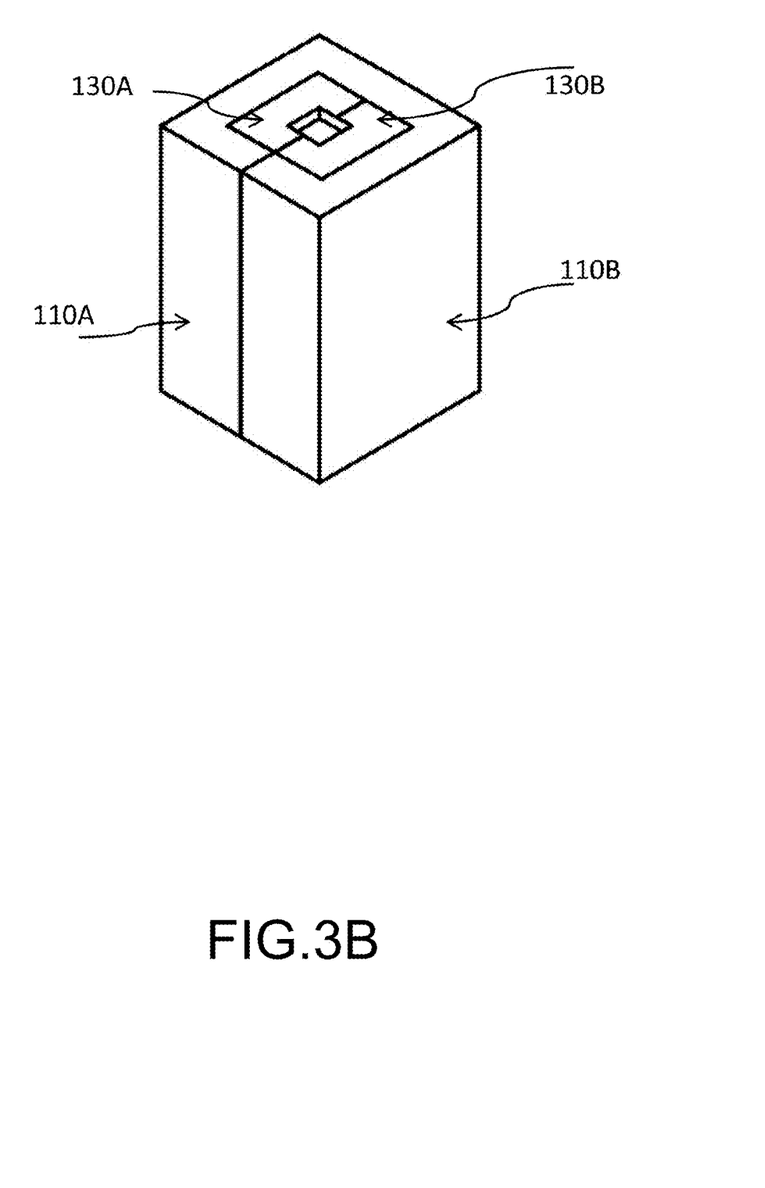
FIG. 3B is an isometric view of a pushed-in electromagnetic wave receiving/transmitting device in accordance with the present invention.

According to a first embodiment of the present invention, as shown in FIGS. 1A, 1B and 2A, the present invention provides an electromagnetic wave receiving/transmitting device 100, which includes: a first base 110A, a second base 110B, a first sensing section 130A, a second sensing section 130B, a front lens 141, a back lens 142, an electromagnetic wave reception processing element 143. Referring to FIG. 1A, the aforementioned first base 110A includes: a first propagation housing space 111A, a first sensing section housing space 112A, a first front opening 113A, a first back opening 114A, a first sensing opening 115A, a first front securing groove 116A, a first back securing groove 117A, a first base sensing section latch 118A, and at least one first base tenon 121A. The aforementioned first sensing section 130A includes: a first identifying housing space 131A, a first sensing section front opening 132A, a first sensing section back opening 133A, and at least one first sensing section stop latch 134A.

According to this embodiment, the aforementioned second base 110B includes: a second propagation housing space 111B, a second sensing section housing space 112B, a second front opening 113B, a second back opening 114B, a second sensing opening 115B, a second front securing groove 116B, a second back securing groove 117B, a second base sensing section latch 118B, and at least one second base mortise 121B. The aforementioned second sensing section 130B includes: a second identifying housing space 131B, a second sensing section front opening 132B, a second sensing section back opening 133B, and at least one second sensing section stop latch 134B.

According to this embodiment, the first propagation housing space 111A is positioned at one end of the first base 110A, whereas the first sensing section housing space 112A is positioned at the other end of the first base 110A. The first propagation housing space 111A and the first sensing section housing space 112A are connected with each other. The first front opening 113A is positioned at one end of the first base 110A and the first propagation housing space 111A, whereas the first sensing opening 115A is positioned at the other end of the first base 110A and the first sensing section housing space 112A, and the first back opening 114A is positioned at a location where the first propagation housing space 111A and the first sensing section housing space 112A are connected. The first front securing groove 116A is positioned at the first front opening 113A, and the first back securing groove 117A is positioned at the first back opening 114A. The first base sensing section latch 118A is positioned at the first sensing opening 115A.

According to this embodiment, the first identifying housing space 131A is positioned at the first sensing section 130A. The first sensing section front opening 132A is positioned at one end of the first sensing section 130A, whereas the first sensing section back opening 133A is positioned at the other end of the first sensing section 130A. The first sensing section stop latch 134A is positioned at the first sensing section back opening 133A, wherein the first sensing section 130A can be latched into the first sensing section housing space 112A. Moreover, the first sensing section 130A is moveable relative to the first sensing section housing space 112A, and the first base sensing section latch 118A and the first sensing section stop latch 134A abut against each other in order to stop the first sensing section 130A from moving out of the first sensing section housing space 112A. The at least one first base tenon 121A is positioned at either sides of the first front opening 113A, the first back opening 114A, the first sensing opening 115A, and the first base 110A.

According to this embodiment, the second propagation housing space 111B is positioned at one end of the second base 110B, whereas the second sensing section housing space 112B is positioned at the other end of the second base 110B. The second propagation housing space 111B and the second sensing section housing space 112B are connected to each other. The second front opening 113B is positioned at one end of the second base 110B and the second propagation housing space 111B, whereas the second sensing opening 115B is positioned at the other end of the second base 110B and the second sensing section housing space 112B, and the second back opening 114B is positioned at a location where the second propagation housing space 111B and the second sensing section housing space 112B are connected. The second front securing groove 116B is positioned at the second front opening 113B, and the second back securing groove 117B is positioned at the second back opening 114B. The second base sensing section latch 118B is positioned at the second sensing opening 115B.

According to this embodiment, the second identifying housing space 131B is positioned at the second sensing section 130B. The second sensing section front opening 132B is positioned at one end of the second sensing section 130B, whereas the second sensing section back opening 133B is positioned at the other end of the second sensing section 130B. The second sensing section stop latch 134B is positioned at the second sensing section back opening 133B, wherein the second sensing section 130B can be latched into the second sensing section housing space 112B. Moreover, the second sensing section 130B is moveable relative to the second sensing section housing space 112B, and the second base sensing section latch 118B and the second sensing section stop latch 134B abut against each other in order to stop the second sensing section 130B from moving out of the second sensing section housing space 112B. The at least one second base mortise 121B is positioned at either sides of the second front opening 113B, the second back opening 114B, the second sensing opening 115B, and the second base 110B.

According to this embodiment, as shown in FIGS. 2A to 3B, the first base 110A, the second base 110B, the first sensing section 130A, the second sensing section 130B are joined together through the first base tenons 121A and the second base mortises 121B. Furthermore, with the structures of the first base tenons 121A and the second base mortises 121B, the two bases can be engaged while preventing side leakage of the propagating electromagnetic waves. The front lens 141 is secured between the first front securing groove 116A and the second front securing groove 116B. The back lens 142 is secured between the first back securing groove 117A and the second back securing groove 117B. The electromagnetic wave reception processing element 143 is secured between the first identifying housing space 131A and the second identifying housing space 131B. The electromagnetic wave receiving/transmitting device 100 further includes at least one emitting element combined onto the electromagnetic wave receiving/transmitting device 100 for emitting electromagnetic waves in the range of 80~550 GHz to properly illuminate the subject, and the range of electromagnetic waves received/propagated by the electromagnetic wave receiving/transmitting device 100 is between 80 to 550 GHz.

According to this embodiment, the material of the first base 110A and the second base 110B includes a filler and a polymer. The filler may include graphite, carbon particles, silver, conductive particles, dyes and pigments. The percentage by weight of the filler to the total weight of the first base 110A and the second base 110B is between 0.5 to 15 wt. %. The polymer may include expanded polypropylene, expanded polystyrene, and polyurethane foam. The percentage by weight of the polymer to the total weight of the first base 110A and the second base 110B is between 85 to 99.5 wt. %. The material of the first base 110A and the second base 110B is an electrically conductive expanded polypropylene. The electrically conductive expanded polypropylene includes carbon particles of a weight percentage between 13 to 15 wt. %. Moreover, the material of the first base 110A and the second base 110B exhibits properties such as high absorption rate, low refractive index, high mechanical strength, and high chemical stability.

Figure 4:
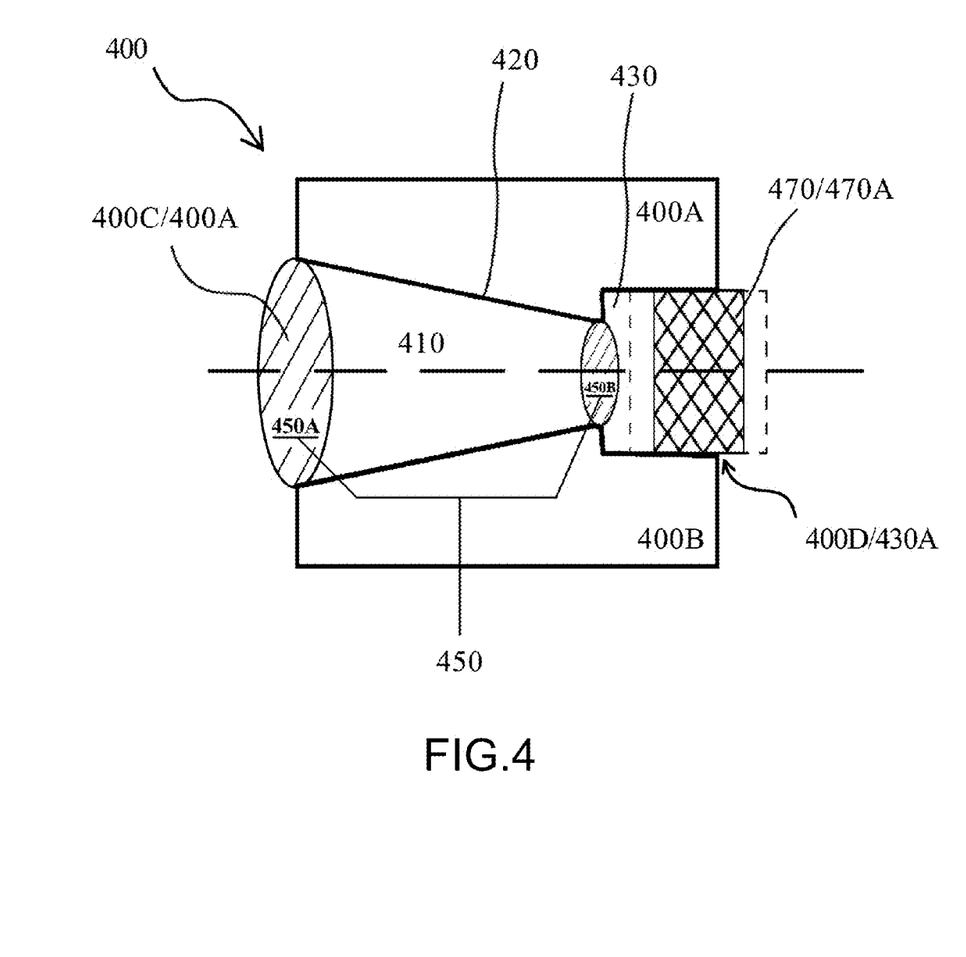
FIG. 4 is a schematic diagram illustrating a physical package for an electromagnetic wave receiving/transmitting device in accordance with the present invention.

According to a second embodiment, as shown in FIG. 4, the present invention includes a physical package 400 for an electromagnetic wave receiving/transmitting device. The physical package 400 for an electromagnetic wave receiving/transmitting device includes an electromagnetic wave propagation cavity 410 and a sensing region 430. The electromagnetic wave propagation cavity 410 is formed from a surrounding wall 420. The surrounding wall 420 is capable of absorbing electromagnetic waves external to the package and the stray electromagnetic waves in the electromagnetic wave propagation cavity 410. One end of the electromagnetic wave propagation cavity 410 is an electromagnetic wave incident port 410A, while the other end of the electromagnetic wave propagation cavity 410 is an electromagnetic wave exit port 410B, wherein the electromagnetic wave incident port 410A is a first opening 400C of the physical package 400. In addition, the sensing region 430 is situated behind the electromagnetic wave exit port 410B and connected with the electromagnetic wave propagation cavity 410 for receiving the electromagnetic waves propagated through the electromagnetic wave exit port 410B. The sensing region 430 is formed by the extension of the surrounding wall 420.

According to this embodiment, the material of the physical package 400 for an electromagnetic wave receiving/transmitting device and its surrounding wall 420 includes a filler and a polymer. The filler may include graphite, carbon particles, silver, conductive particles, dyes and pigments, and the percentage by weight of the filler to the total weight of the physical package 400 and its surrounding wall 420 is between 0.5 to 15 wt. %. Furthermore, the polymer may include expanded polypropylene, expanded polystyrene and polyurethane foam. The percentage by weight of the polymer to the total weight of the surrounding wall is between 85 to 99.5 wt. %. The material of the surrounding wall is an electrically conductive expanded polypropylene. The electrically conductive expanded polypropylene includes carbon particles of a weight percentage between 13 to 15 wt. %.

The material of the aforementioned physical package 400 and its surrounding wall 420 has low refractive index. Preferably, its refractive index is about 1.0, so it not only minimizes internal reflections but also absorbs both the external electromagnetic waves and the stray electromagnetic waves generated inside the electromagnetic wave propagation cavity, thereby eliminating interference from noises in the electromagnetic wave propagation cavity and effectively propagating high-frequency electromagnetic waves while maintaining a high signal-to-noise ratio.

The aforementioned material includes a foamed structure and a filler at a specific ratio, thus exhibiting high mechanical strength. Meanwhile, the aforementioned material also has high chemical stability, so when used as a packaging material, it can protect the internal elements of the electromagnetic wave receiving/transmitting device of the present invention from physical or chemical detriment or both.

According to the descriptions above, the packaging material proposed by the present invention has properties of high absorption rate, low refractive index, high mechanical strength and high chemical stability, and compared to normal materials, it is particularly suitable for use as a packaging material for the electromagnetic wave receiving/transmitting device of the present invention.

According to this embodiment, the physical package 400 further includes a first outer casing 400A and a second outer casing 400B. The outer walls of the first outer casing 400A and the second outer casing 400B are conformally formed and sealed, while the inner walls of the first outer casing 400A and the second outer casing 400B are conformally formed as the surrounding wall 420. The appearance of the outer walls of the first outer casing 400A and the second outer casing 400B can be nonlinear or uneven in order to prevent side leakage of electromagnetic waves. The joining surfaces between the outer walls of the first outer casing 400A and the second outer casing 400B further include matching concave/convex features for fastening purpose as well as preventing side leakage of electromagnetic waves.

According to this embodiment, the electromagnetic wave receiving/transmitting device further includes a lens assembly 450. The lens assembly 450 is provided in the electromagnetic wave propagation cavity 410 of the physical package 400. The aforementioned lens assembly 450 further includes: an incident lens 450A located at the electromagnetic wave incident port 410A for guiding the electromagnetic waves into the electromagnetic wave propagation cavity 410; and an outgoing lens 450B located at the electromagnetic wave exit port 410B for guiding the electromagnetic waves out of the electromagnetic wave propagation cavity 410 and into the sensing region 430. The electromagnetic wave propagation cavity 410 has a conical shape, wherein the electromagnetic wave incident port 410A is bigger than the electromagnetic wave exit port 410B, and the sizes and shapes of the incident lens 450A and the outgoing lens 450B are conformal to the electromagnetic wave incident port 410A and the electromagnetic wave exit port 410B, respectively.

According to this embodiment, the electromagnetic wave receiving/transmitting device further includes a sensing assembly 470. The sensing assembly 470 is provided in the sensing region 430 for sensing the electromagnetic waves coming out of the electromagnetic wave exit port 410B to facilitate electromagnetic wave imaging. The sensing assembly 470 further includes a carrier 470A for carrying a sensing analyzing element. The carrier 470A is able to modify the imaging focal length by displacement movements. The direction of the displacement movement of the aforementioned carrier 470A is the same as the incident direction of the electromagnetic waves. The aforementioned sensing region 430 further includes a displacement opening 430A. The displacement opening 430A is a second opening 400D of the physical package, wherein the displacement opening 430A is provided at an opposite location to the electromagnetic wave incident port 410A of the physical package, so as to allow the carrier 470A to carry out displacement movements for adjusting the imaging focal length in the displacement opening 430A.

According to this embodiment, the physical package 400 further includes at least one electromagnetic wave emitting unit 480 for emitting electromagnetic waves of frequencies between 80~550 GHz. The electromagnetic wave emitting unit 480 can be mounted on the outer surface of the physical package 400, and the frequency range of electromagnetic waves received by the electromagnetic wave receiving/transmitting device is between 80 to 550 GHz.

According to a third embodiment of the present invention, as shown in FIG. 4, the present invention provides an electromagnetic wave imaging method, which includes: generating an electromagnetic wave in the range of 80 to 550 GHz by at least one electromagnetic wave emitting unit 480. Then, the electromagnetic wave illuminates on objects to be measured, M and N, at specific locations, forming a projected electromagnetic wave. Next, the projected electromagnetic wave is guided through the electromagnetic wave incident port 410A into the electromagnetic wave propagation cavity 410 to form an incident electromagnetic wave. The projected electromagnetic wave includes the electromagnetic wave generated by the electromagnetic wave emitting unit in addition to other external stray electromagnetic waves. The electromagnetic wave propagation cavity is formed from the surrounding wall 420. The surrounding wall 420 is capable of absorbing the external electromagnetic wave and the stray electromagnetic waves in the electromagnetic wave propagation cavity 410, allowing the incident electromagnetic wave to form a captured electromagnetic wave, wherein the electromagnetic wave incident port 410A further includes the incident lens 450A for guiding the external electromagnetic wave into the electromagnetic wave propagation cavity 410, wherein the electromagnetic wave propagation cavity 410 has a conical shape, and the electromagnetic wave incident port 410A is larger than the electromagnetic wave exit port 410B.

According to this embodiment, the captured electromagnetic wave is guided out of the electromagnetic wave exit port 410B of the electromagnetic wave propagation cavity 410 to a sensing region 430. The sensing region 430 is connected with the electromagnetic wave propagation cavity 410 to receive the captured electromagnetic wave, and the sensing region 430 is formed by the extension of the surrounding wall 420, wherein the electromagnetic wave exit port 410B further includes the outgoing lens 450B that optimizes the guiding of the captured electromagnetic wave from the electromagnetic wave propagation cavity 410 into the sensing region.

According to this embodiment, the incident electromagnetic wave is detected and analyzed to form an image by a sensing imaging device 470, wherein the sensing imaging device 470 is provided in the aforementioned sensing region 430. The sensing imaging device is capable of performing displacement movements in the sensing region to adjust the focus, wherein the direction of the displacement movement is the same as the incident direction of the electromagnetic wave.

Figure 5A:
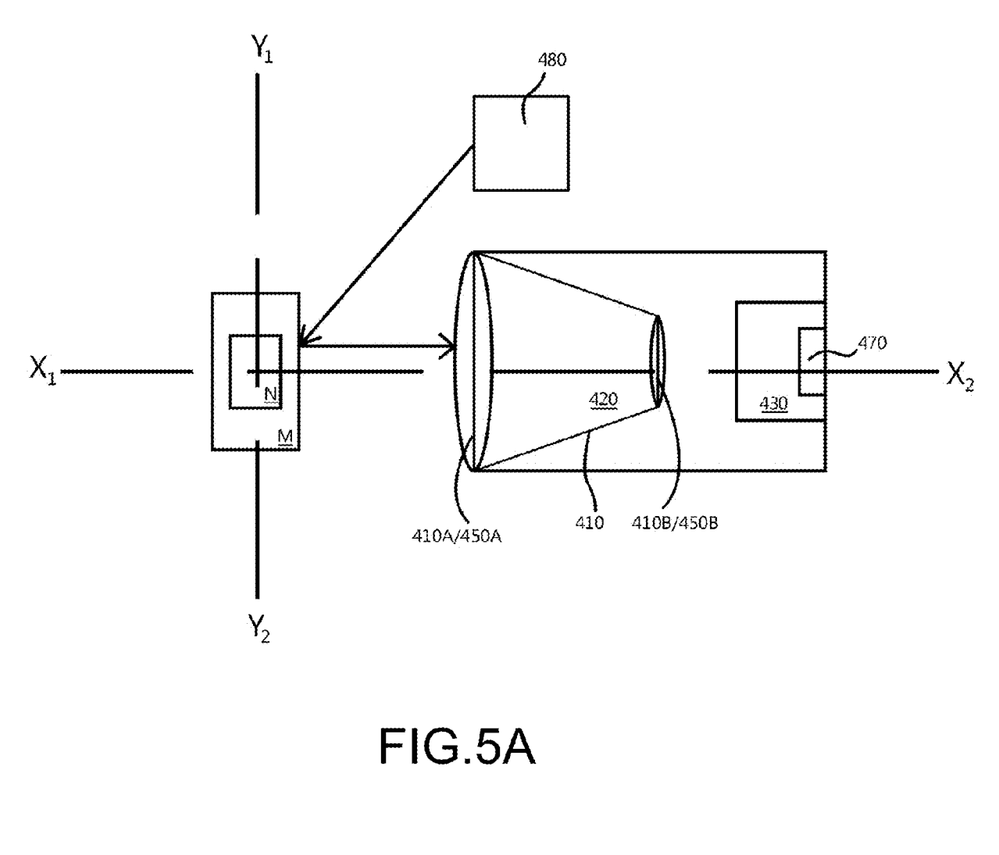
FIG. 5A is a schematic diagram illustrating reflective electromagnetic wave reception/transmission in accordance with the present invention.

According to this embodiment, as shown in FIG. 5A, the electromagnetic wave imaging method of the present invention is a reflective electromagnetic wave imaging method. The electromagnetic wave emitting unit 480 and the electromagnetic wave incident port 410A are on the same side X2 of the reference coordinate axis Y1-Y2 shown in FIG. 5A. The electromagnetic wave of the electromagnetic wave emitting unit 480 is emitted along the direction from X2 to X1, and is reflected by the different objects to be measured M and N to form a reflected electromagnetic wave. The reflected electromagnetic wave is reflected along the direction from X1 to X2 into the electromagnetic wave propagation cavity 410. In other words, the electromagnetic wave emitting unit 480 and the electromagnetic wave incident port 410A are on opposite directions along which electromagnetic waves propagate, wherein the reflected electromagnetic wave is the projected electromagnetic wave. The different objects to be measured, namely M and N, may be on the same measuring location, such that one surrounds the other or their locations overlap. For example, M is larger than N in size, and M surrounds N. The same measuring location means that the objects are on the same reference coordinate axis Y1-Y2. The reflective electromagnetic wave imaging method of the present invention is able to detect and analyze the incident electromagnetic wave using the sensing imaging device 470 in order to form images of different intensities for different objects to be measured M and N.

Figure 5B:
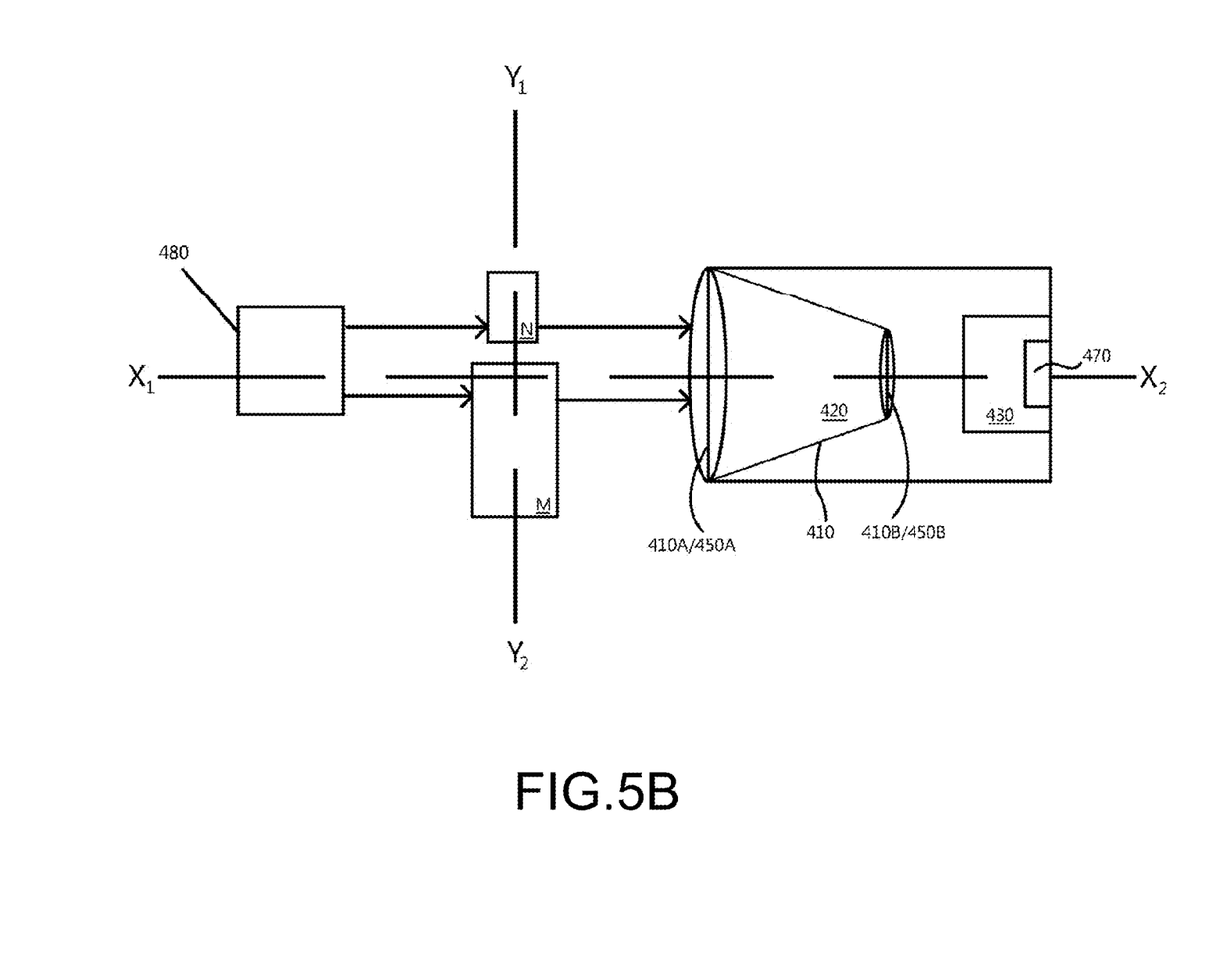
FIG. 5B is a schematic diagram illustrating transmissive electromagnetic wave reception/transmission in accordance with the present invention.

According to this embodiment, as shown in FIG. 5B, the electromagnetic wave imaging method of the present invention is a transmissive electromagnetic wave imaging method. The electromagnetic wave emitting unit 480 and the electromagnetic wave incident port 410A are on the two sides X1 and X2 of the reference coordinate axis Y1-Y2 shown in FIG. 5B. The electromagnetic wave of the electromagnetic wave emitting unit 480 is emitted along the direction from X1 to X2, and forms a transmissive electromagnetic wave from the different objects to be measured M and N. The different objects to be measured M and N can be on the same measuring locations. The transmissive electromagnetic wave is transmitted along the direction from X1 to X2 into the electromagnetic wave propagation cavity 410. In other words, the electromagnetic wave emitting unit 480 and the electromagnetic wave incident port 410A are on the same direction along which electromagnetic waves propagate, wherein the transmissive electromagnetic wave is the projected electromagnetic wave. The same measuring location means that the objects are on the same reference coordinate axis Y1-Y2. The transmissive electromagnetic wave imaging method of the present invention is able to sense and analyze the incident electromagnetic wave using the sensing imaging device 470 in order to form images of different intensities of the different objects to be measured M and N.

According to this embodiment, with reference to FIGS. 5A and 5B, the present invention may also have a plurality of the electromagnetic wave emitting units 480 provided at different specific locations, allowing both reflective and transmissive imaging methods to be performed at the same time.

According to this embodiment, the packaging material of the aforementioned surrounding wall 420 includes a filler. The filler may include graphite, carbon particles, silver, conductive particles, dyes and pigments. The percentage by weight of the filler to the total weight of the surrounding wall is between 0.5 to 15 wt. %. The packaging material of the surrounding wall includes a polymer, which may further include expanded polypropylene, expanded polystyrene and polyurethane foam. The percentage by weight of the polymer to the total weight of the surrounding wall is between 85 to 99.5 wt. %. The material of the surrounding wall is an electrically conductive expanded polypropylene. The electrically conductive expanded polypropylene includes carbon particles of a weight percentage between 13 to 15 wt. %. Moreover, the material of the surrounding wall 420 exhibits low refractive index. Preferably, its refractive index is about 1.0; Therefore, it not only minimizes internal reflections, but also absorbs both the external electromagnetic waves and the stray electromagnetic waves generated inside the electromagnetic wave propagation cavity, thereby eliminating interference from noises in the electromagnetic wave propagation cavity and effectively propagating high-frequency electromagnetic waves while maintaining a high signal-to-noise ratio.

In summary, it is apparent that, in light of the description of the above embodiments, various modifications and variations of the present invention are possible. Therefore, the present invention should be interpreted under the scope of the appended claims. In addition to the above detailed description, the present invention can also be widely embodied in other embodiments. The above descriptions are merely provided to illustrate preferred embodiments of the present invention, and are not intended to limit the claims of the present invention in any way. Any equivalent changes or modifications made without departing from the spirit of the present invention should be construed as being included in the following claims.

What is claimed is:

1. An electromagnetic wave receiving/transmitting device, comprising:
    a first base, a first propagation housing space positioned at one end of the first base, a first sensing section housing space positioned at the other end of the first base, and the first propagation housing space and the first sensing section housing space being connected with each other, wherein a first front opening is positioned at one end of the first base and the first propagation housing space, a first sensing opening is positioned at the other end of the first base and the first sensing section housing space, and a first back opening is positioned at a location where the first propagation housing space and the first sensing section housing space are connected, wherein a first front securing groove is positioned at the first front opening, a first back securing groove is positioned at the first back opening, and the first base sensing section latch is positioned at the first sensing opening, wherein at least one first base tenon is positioned at either sides of the first front opening, the first back opening, the first sensing opening, and the first base;
    a second base, a second propagation housing space positioned at one end of the second base, a second sensing section housing space positioned at the other end of the second base, and the second propagation housing space and the second sensing section housing space being connected with each other, wherein a second front opening is positioned at one end of the second base and the second propagation housing space, a second sensing opening is positioned at the other end of the second base and the second sensing section housing space, and a second back opening is positioned at a location where the second propagation housing space and the second sensing section housing space are connected, wherein a second front securing groove is positioned at the second front opening, and a second back securing groove is positioned at the second back opening, and a second base sensing section latch is positioned at the second sensing opening, wherein at least one second base mortise is positioned at either sides of the second front opening, the second back opening, the second sensing opening, and the second base;
    a first sensing section, a first identifying housing space positioned at the first sensing section, wherein the first sensing section front opening is positioned at one end of the first sensing section, a first sensing section back opening is positioned at the other end of the first sensing section, wherein a first sensing section stop latch is positioned at the first sensing section back opening, wherein the first sensing section is capable of being latched into the first sensing section housing space, wherein the first sensing section is moveable relative to the first sensing section housing space, and the first base sensing section latch and the first sensing section stop latch abut against each other in order to stop the first sensing section from moving out of the first sensing section housing space; and
    a second sensing section, a second identifying housing space positioned at the second sensing section, wherein a second sensing section front opening is positioned at one end of the second sensing section, a second sensing section back opening is positioned at the other end of the second sensing section, wherein a second sensing section stop latch is positioned at the second sensing section back opening, wherein the second sensing section is capable of being latched into the second sensing section housing space, wherein the second sensing section is moveable relative to the second sensing section housing space, and the second base sensing section latch and the second sensing section stop latch abut against each other in order to stop the second sensing section from moving out of the second sensing section housing space, wherein the first base, the second base, the first sensing section, and the second sensing section are joined together by the at least one first base tenon and the at least one second base mortise.

2. The electromagnetic wave receiving/transmitting device of claim 1, further comprising at least one emitting element combined with the electromagnetic wave receiving/transmitting device for emitting electromagnetic waves in the range of 80 to 550 GHz.

3. The electromagnetic wave receiving/transmitting device of claim 1, further comprising a front lens secured between the first front securing groove and the second front securing groove.

4. The electromagnetic wave receiving/transmitting device of claim 1, further comprising a back lens secured between the first back securing groove and the second back securing groove.

5. The electromagnetic wave receiving/transmitting device of claim 1, further comprising an electromagnetic wave reception processing element secured between the first identifying housing space and the second identifying housing space.

6. The electromagnetic wave receiving/transmitting device of claim 1, wherein the material of the first base and the second base includes a filler, the filler includes graphite, carbon particles, silver, conductive particles, dyes and pigments, and the percentage by weight of the filler to the total weight of the first base and the second base is between 0.5 to 15 wt. %.

7. The electromagnetic wave receiving/transmitting device of claim 1, wherein the material of the first base and the second base exhibits high absorption rate, low refractive index, high mechanical strength and high chemical stability.

8. The electromagnetic wave receiving/transmitting device of claim 1, wherein the material of the first base and the second base includes a polymer, the polymer includes expanded polypropylene, expanded polystyrene and polyurethane foam, and the percentage by weight of the polymer to the total weight of the first base and the second base is between 85 to 99.5 wt. %.

9. The electromagnetic wave receiving/transmitting device of claim 8, wherein the material of the first base and the second base is an electrically conductive expanded polypropylene, the electrically conductive expanded polypropylene includes carbon particles of a weight percentage between 13 to 15 wt. %.

10. The electromagnetic wave receiving/transmitting device of claim 1, wherein the range of electromagnetic waves received/propagated by the electromagnetic wave receiving/transmitting device is between 80 and 550 GHz.

11. A physical package for an electromagnetic wave receiving/transmitting device, comprising:
an electromagnetic wave propagation cavity formed from a surrounding wall, the surrounding wall being capable of absorbing electromagnetic waves external to the package and stray electromagnetic waves in the electromagnetic wave propagation cavity, one end of the electromagnetic wave propagation cavity being an electromagnetic wave incident port, and the other end of the electromagnetic wave propagation cavity being an electromagnetic wave exit port, wherein the electromagnetic wave incident port is a first opening of the physical package; and
a sensing region situated behind the electromagnetic wave exit port and in communication with the electromagnetic wave propagation cavity for receiving electromagnetic waves propagated by the electromagnetic wave exit port, and the sensing region being formed from the extension of the surrounding wall.

12. The physical package for an electromagnetic wave receiving/transmitting device of claim 11, wherein the range of electromagnetic waves received by the electromagnetic wave receiving/transmitting device is between 80 and 550 GHz.

13. The physical package for an electromagnetic wave receiving/transmitting device of claim 11, wherein the material of the physical package and the surrounding wall includes a filler, the filler includes graphite, carbon particles, silver, conductive particles, dyes and pigments, and the percentage by weight of the filler to the total weight of the surrounding wall is between 0.5 to 15 wt. %.

14. The physical package for an electromagnetic wave receiving/transmitting device of claim 11, wherein the material of the physical package and the surrounding wall includes a polymer, the polymer includes expanded polypropylene, expanded polystyrene and polyurethane foam, and the percentage by weight of the polymer to the total weight of the surrounding wall is between 85 to 99.5 wt. %.

15. The physical package for an electromagnetic wave receiving/transmitting device of claim 14, wherein the material of the physical package and the surrounding wall includes an electrically conductive expanded polypropylene, the electrically conductive expanded polypropylene includes carbon particles of a weight percentage between 13 to 15 wt. %.

16. The physical package for an electromagnetic wave receiving/transmitting device of claim 11, wherein the material of the physical package and the surrounding wall exhibit high absorption rate, low refractive index, high mechanical strength and high chemical stability.

17. The physical package for an electromagnetic wave receiving/transmitting device of claim 11, further comprising a first outer casing and a second outer casing, the outer walls of the first outer casing and the second outer casing being conformally formed and sealed, while the inner walls of the first outer casing and the second outer casing being conformally formed as the surrounding wall.

18. The physical package for an electromagnetic wave receiving/transmitting device of claim 17, wherein the appearance of the outer walls of the first outer casing and the second outer casing is nonlinear or uneven in order to prevent side leakage of electromagnetic waves.

19. The physical package for an electromagnetic wave receiving/transmitting device of claim 17, wherein the joining surfaces between the outer walls of the first outer casing and the second outer casing further include matching concave/convex features for fastening purpose as well as preventing side leakage of electromagnetic waves.

20. The physical package for an electromagnetic wave receiving/transmitting device of claim 11, wherein the electromagnetic wave receiving/transmitting device further includes a lens assembly provided in the electromagnetic wave propagation cavity of the physical package.

21. The physical package for an electromagnetic wave receiving/transmitting device of claim 20, wherein the lens assembly further includes:
an incident lens located at the electromagnetic wave incident port for guiding the electromagnetic waves into the electromagnetic wave propagation cavity; and
an outgoing lens located at the electromagnetic wave exit port for guiding the electromagnetic waves out of the electromagnetic wave propagation cavity and into the sensing region.

22. The physical package for an electromagnetic wave receiving/transmitting device of claim 11, wherein the electromagnetic wave propagation cavity has a conical shape, wherein the electromagnetic wave incident port is larger than the electromagnetic wave exit port, and the sizes and shapes of the incident lens and the outgoing lens are conformal to the electromagnetic wave incident port and the electromagnetic wave exit port, respectively.

23. The physical package for an electromagnetic wave receiving/transmitting device of claim 11, wherein the electromagnetic wave receiving/transmitting device further includes a sensing assembly provided in the sensing region for sensing the electromagnetic waves coming out of the electromagnetic wave exit port to facilitate electromagnetic wave imaging.

24. The physical package for an electromagnetic wave receiving/transmitting device of claim 23, wherein the sensing assembly further includes a carrier for carrying a sensing analyzing element, the carrier is able to modify the imaging focal length by displacement movements, wherein the direction of the displacement movement of the carrier is the same as the incident direction of the electromagnetic waves.

25. The physical package for an electromagnetic wave receiving/transmitting device of claim 24, wherein the sensing region further includes a displacement opening, the displacement opening is a second opening of the physical package, wherein the displacement opening is provided at an opposite location to the electromagnetic wave incident port of the physical package to allow the carrier to carry out displacement movements in the displacement opening for adjusting the imaging focus distance.

26. The physical package for an electromagnetic wave receiving/transmitting device of claim 11, further comprising an electromagnetic wave emitting unit to illuminate objects to be measured, the electromagnetic wave emitting unit and the physical package being located on opposite propagation directions of the electromagnetic waves.

27. An electromagnetic wave imaging method, comprising:
   forming a projected electromagnetic wave from an electromagnetic wave reflected off one or more objects to be measured;
   guiding the projected electromagnetic wave through an electromagnetic wave incident port into an electromagnetic wave propagation cavity to form an incident electromagnetic wave, the electromagnetic wave propagation cavity formed by a surrounding wall capable of absorbing stray electromagnetic waves from outside and inside the electromagnetic wave propagation cavity, allowing the incident electromagnetic wave to form a captured electromagnetic wave;
   guiding the sensing electromagnetic wave through an electromagnetic wave exit port out of the electromagnetic wave propagation cavity to a sensing region connected with the electromagnetic wave propagation cavity for receiving the captured electromagnetic wave, and the sensing region being formed by the extension of the surrounding wall; and
   detecting and analyzing the captured electromagnetic wave to form an image by a sensing imaging device provided in the sensing region.

28. The electromagnetic wave imaging method of claim 27, wherein the electromagnetic wave incident port further includes an incident lens for guiding an external electromagnetic wave into the electromagnetic wave propagation cavity.

29. The electromagnetic wave imaging method of claim 27, wherein the electromagnetic wave exit port further includes an outgoing lens for guiding the captured electromagnetic wave out of the electromagnetic wave propagation cavity and into the sensing region.

30. The electromagnetic wave imaging method of claim 27, wherein the electromagnetic wave propagation cavity has a conical shape, wherein the electromagnetic wave incident port is larger than the electromagnetic wave exit port.

31. The electromagnetic wave imaging method of claim 27, wherein the material of the surrounding wall includes a filler, the filler includes graphite, carbon particles, silver, conductive particles, dyes and pigments, and the percentage by weight of the filler to the total weight of the surrounding wall is between 0.5 to 15 wt. %.

32. The electromagnetic wave imaging method of claim 27, wherein the material of the surrounding wall includes a polymer, the polymer includes expanded polypropylene, expanded polystyrene and polyurethane foam, and the percentage by weight of the polymer to the total weight of the surrounding wall is between 85 to 99.5 wt. %.

33. The electromagnetic wave imaging method of claim 32, wherein the material of the surrounding wall includes an electrically conductive expanded polypropylene, the electrically conductive expanded polypropylene includes carbon particles of a weight percentage between 13 to 15 wt. %.

34. The electromagnetic wave imaging method of claim 27, wherein the sensing imaging device is capable of performing displacement movements in the sensing region to adjust the imaging focus distance, wherein the direction of the displacement movement is the same as the incident direction of the electromagnetic wave.

35. The electromagnetic wave imaging method of claim 27, further comprising at least one electromagnetic wave emitting unit, the frequency range of the electromagnetic wave is between 80 and 550 GHz.

36. The electromagnetic wave imaging method of claim 35, wherein the electromagnetic wave is illuminated onto the object to be measured at a specific measuring location, and the projected electromagnetic wave is formed from the electromagnetic wave reflected off the object to be measured.

37. The electromagnetic wave imaging method of claim 36, wherein the electromagnetic wave imaging method is a reflective electromagnetic wave imaging method, the electromagnetic wave emitting unit and the electromagnetic wave incident port are on opposite propagation directions of the electromagnetic wave.

38. The electromagnetic wave imaging method of claim 36, the electromagnetic wave imaging method is a transmissive electromagnetic wave imaging method, the electromagnetic wave emitting unit and the electromagnetic wave incident port are on the same propagation direction of the electromagnetic wave.

* * * * *